United States Patent
Leslie et al.

(10) Patent No.: US 7,711,177 B2
(45) Date of Patent: May 4, 2010

(54) METHODS AND SYSTEMS FOR DETECTING DEFECTS ON A SPECIMEN USING A COMBINATION OF BRIGHT FIELD CHANNEL DATA AND DARK FIELD CHANNEL DATA

(75) Inventors: Brian Leslie, Cupertino, CA (US); Ashok Kulkarni, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 864 days.

(21) Appl. No.: 11/422,955

(22) Filed: Jun. 8, 2006

(65) Prior Publication Data

US 2007/0286473 A1    Dec. 13, 2007

(51) Int. Cl.
*G06K 9/00* (2006.01)
*G01N 37/00* (2006.01)
*G01D 3/00* (2006.01)

(52) U.S. Cl. .................. 382/141; 382/144; 702/81; 702/108

(58) Field of Classification Search .............. 382/141, 382/144; 702/81, 108
See application file for complete search history.

(56) References Cited

U.S. PATENT DOCUMENTS

| | | | |
|---|---|---|---|
| 6,104,835 A | 8/2000 | Han | |
| 6,650,779 B2 | 11/2003 | Vachtesvanos et al. | |
| 6,804,381 B2 | 10/2004 | Pang et al. | |
| 6,855,930 B2 | 2/2005 | Okuda et al. | |
| 7,286,218 B2 | 10/2007 | Tiemeyer et al. | |

(Continued)

FOREIGN PATENT DOCUMENTS

WO    99/67626    12/1999

OTHER PUBLICATIONS

International Search Report and Written Opinion for PCT/US07/70749 filed on June 8, 2007.

(Continued)

*Primary Examiner*—Samir A. Ahmed
*Assistant Examiner*—Fred Hu
(74) *Attorney, Agent, or Firm*—Ann Marie Mewherter

(57) ABSTRACT

Various methods, carrier media, and systems for detecting defects on a specimen using a combination of bright field channel data and dark field channel data are provided. One computer-implemented method includes combining pixel-level data acquired for the specimen by a bright field channel and a dark field channel of an inspection system. The method also includes detecting defects on the specimen by applying a two-dimensional threshold to the combined data. The two-dimensional threshold is defined as a function of a threshold for the data acquired by the bright field channel and a threshold for the data acquired by the dark field channel.

22 Claims, 3 Drawing Sheets

U.S. PATENT DOCUMENTS

| | | | |
|---|---|---|---|
| 2002/0107650 A1* | 8/2002 | Wack et al. | 702/81 |
| 2004/0091142 A1* | 5/2004 | Peterson et al. | 382/144 |
| 2004/0165762 A1* | 8/2004 | Messina et al. | 382/141 |
| 2005/0004774 A1* | 1/2005 | Volk et al. | 702/108 |
| 2005/0062962 A1 | 3/2005 | Fairley et al. | |
| 2006/0062445 A1 | 3/2006 | Verma et al. | |
| 2006/0069460 A1 | 3/2006 | Smith et al. | |
| 2006/0192950 A1 | 8/2006 | Judell et al. | |
| 2007/0121106 A1* | 5/2007 | Shibata et al. | 356/237.2 |
| 2007/0273878 A1* | 11/2007 | Fujii et al. | 356/337 |
| 2009/0091749 A1* | 4/2009 | Furman et al. | 356/237.2 |

OTHER PUBLICATIONS

U.S. Appl. No. 11/005,658 entitled Computer-Implemented Methods for Detecting and/or Sorting Defects in a Design Pattern of a Reticle, filed Dec. 7, 2004.

U.S. Appl. No. 60/738,290 entitled Methods and Systems for Utilizing Design Data in Combination With Inspection Data, filed Nov. 18, 2005.

U.S. Appl. No. 11/300,172 entitled Methods and Systems for Binning Defects Detected on a Specimen, filed Dec. 14, 2005.

* cited by examiner

METHODS AND SYSTEMS FOR DETECTING DEFECTS ON A SPECIMEN USING A COMBINATION OF BRIGHT FIELD CHANNEL DATA AND DARK FIELD CHANNEL DATA

BACKGROUND OF THE INVENTION

1. Field of the Invention

The present invention generally relates to methods and systems for detecting defects on a specimen using a combination of bright field channel data and dark field channel data. Certain embodiments relate to combining pixel-level data acquired for a specimen by a bright field channel and a dark field channel of an inspection system and detecting defects on the specimen by applying a two-dimensional threshold to the combined data.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits (ICs). However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Inspection for many different types of defects has also become more important recently. For instance, in order to use inspection results to monitor and correct semiconductor fabrication processes, it is often necessary to know what types of defects are present on a specimen. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

In order for inspection to provide useful results for yield control, the inspection process must be able to not only detect many different kinds of defects but also to discriminate between real defects on the wafer or reticle and noise or nuisance events. Noise may be defined as events detected on a wafer or reticle by an inspection tool that are not actually defects but appear as potential defects due to marginalities in the inspection tool such as marginalities in data processing and/or data acquisition. Nuisance events are actual defects but that are not relevant to the user for the purposes of controlling the process or predicting yield. Moreover, the same defect may be considered a nuisance event at one point in time, but it may later be found to be a relevant defect. In some instances, the number of noise and nuisance events detected by an inspection tool can be reduced by using optimized data acquisition parameters and optimized data processing parameters. In addition, the number of noise and nuisance events can be reduced by applying various filtering techniques to the inspection results.

As design rules shrink, however, semiconductor manufacturing processes may be operating closer to the limitations on the performance capability of the processes. In addition, smaller defects can have an impact on the electrical characteristics of the device as the design rules shrink, which drives more sensitive inspections. Therefore, as design rules shrink, the population of potentially yield relevant defects detected by inspection grows dramatically, and the population of nuisance defects detected by inspection also increases dramatically. Consequently, more and more defects may be detected on the wafers, and correcting the manufacturing processes to eliminate all of the defects may be difficult and expensive. As such, determining which of the defects actually have an effect on the electrical characteristics of the devices and the yield may allow process control methods to be focused on those defects while largely ignoring others. Furthermore, at smaller design rules, process induced failures may, in some cases, tend to be systematic. That is, process induced failures tend to fail at predetermined design patterns often repeated many times within the design. Elimination of spatially systematic, electrically relevant defects is important because eliminating such defects can have a significant overall impact on yield.

Classifying defects found on wafers and other specimens has, therefore, become increasingly important in order to determine what kinds of defects are present on the wafers in addition to distinguishing the defect types of interest from other defect types. Several fully automatic defect classification (ADC) tools are now available. Typically, these tools use classification "recipes" to perform defect classification. A "recipe" can be generally defined as a set of instructions that define an operation to be performed by a tool and that are provided to and run on the tool upon request by a user. Classification recipes are typically generated using previous data acquired for specific defect classes that may be assembled in a suitable database. In the simplest implementation, the ADC tool can then compare unknown defects to those included in the specific defect classes to determine which defect class the unknown defect is most like. Obviously, much more complicated algorithms can be used by the ADC tool to determine which of the defect classes the unknown defect most likely belongs to.

Sometimes ADC is performed after inspection of a wafer. However, some systems and methods have been developed that can be used to perform ADC during inspection or "on-the-fly." Examples of such systems and methods are illustrated in International Publication No. WO 99/67626 by Ravid et al., which is incorporated by reference as if fully set forth herein. The systems and methods described in this publication are generally configured to separately detect defects in the electrical signals produced by different detectors. In other words, the electrical signals produced by each of the detectors are processed separately to determine if each detector has detected a defect. At any time that a defect is detected in the electrical signals produced by one of the detectors, the electrical signals produced by at least two of the detectors are analyzed collectively to determine scattered light attributes of the defect such as reflected light intensity, reflected light volume, reflected light linearity, and reflected light asymmetry. The defect is then classified (e.g., as a pattern defect or a particle defect) based on these attributes.

Although the methods and systems disclosed in the above-referenced publication utilize scattered light attributes of defects determined from electrical signals generated by more than one detector, the methods and systems disclosed in this publication do not utilize electrical signals generated by more than one detector in combination to detect the defects. In addition, the methods and systems disclosed in this publication do not use a combination of electrical signals generated by more than one detector for any defect-related function other than classification. Other currently available inspection systems are configured to inspect a specimen with more than one detection channel, to detect defects on the specimen by separately processing the data acquired by each of the channels, and to classify the defects by separately processing the data acquired by each of the channels. The defects detected by each of the individual channels may also be further processed separately, for example, by generating different wafer maps, each illustrating the defects detected by only one of the individual channels. The results generated by more than one channel of such a system may then be combined using, for example, Venn addition of the individual wafer maps.

Accordingly, it would be advantageous to develop methods and systems that utilize data generated by more than one detection channel of an inspection system to detect defects on a specimen thereby increasing the signal-to-noise ratio of defect detection and/or to perform one or more other defect-related functions thereby increasing the sensitivity, accuracy, and/or precision of the defect-related functions.

SUMMARY OF THE INVENTION

The following description of various embodiments of methods, carrier media, and systems is not to be construed in any way as limiting the subject matter of the appended claims.

One embodiment relates to a computer-implemented method for detecting defects on a specimen. The method includes combining pixel-level data acquired for the specimen by a bright field (BF) channel and a dark field (DF) channel of an inspection system. The method also includes detecting defects on the specimen by applying a two-dimensional threshold to the combined data. The two-dimensional threshold is defined as a function of a threshold for the data acquired by the BF channel and a threshold for the data acquired by the DF channel.

In one embodiment, the data is acquired by the BF channel and the DF channel in the deep ultraviolet (DUV) spectrum. In another embodiment, applying the two-dimensional threshold to the combined data results in a signal-to-noise ratio for detecting the defects that is higher than a signal-to-noise ratio for detecting the defects by applying the threshold for the data acquired by the BF channel to the pixel-level data acquired by the BF channel and by applying the threshold for the data acquired by the DF channel to the pixel-level data acquired by the DF channel. In an additional embodiment, the defects detected using the two-dimensional threshold include fewer nuisance defects than defects detected by applying the threshold for the data acquired by the BF channel to the pixel-level data acquired by the BF channel and by applying the threshold for the data acquired by the DF channel to the pixel-level data acquired by the DF channel.

In some embodiments, the method includes generating the pixel-level data by subtracting BF reference data from raw data acquired by the BF channel and subtracting DF reference data from raw data acquired by the DF channel. In another embodiment, the method includes classifying the defects using one or more characteristics of the combined data corresponding to the defects, one or more characteristics of patterned features formed on the specimen proximate to the defects determined from the pixel-level data acquired by the BF channel, one or more characteristics of the patterned features formed on the specimen proximate to the defects determined from the pixel-level data acquired by the DF channel, or some combination thereof.

In one embodiment, the method includes altering the threshold for the data acquired by the BF or DF channel based on the pixel-level data acquired by the DF or BF channel, respectively. In another embodiment, the method includes using the pixel-level data acquired by the BF channel to align the pixel-level data acquired by the BF channel to design data for the specimen and altering the threshold for the data acquired by the BF channel based on the design data. In a further embodiment, the method includes using the pixel-level data acquired by the BF channel to align the pixel-level data acquired by the DF channel to design data for the specimen and altering the threshold for the data acquired by the DF channel based on the design data.

In one embodiment, the method includes identifying patterned features formed on the specimen using the pixel-level data acquired by the BF channel, separating the data acquired by the DF channel into different segments based on the patterned features, and altering the threshold for the data acquired by the DF channel for the different segments based on the patterned features. In another embodiment, the method includes identifying patterned features formed on the specimen using the pixel-level data acquired by the DF channel, separating the data acquired by the BF channel into different segments based on the patterned features, and altering the threshold for the data acquired by the BF channel based on the patterned features.

In one embodiment, the pixel-level data acquired by the BF channel includes image data. In one such embodiment, the method includes comparing the image data to reference templates corresponding to different regions of the specimen to determine if the reference templates match the image data and using the image data matched to the reference templates to determine portions of the pixel-level data acquired by the DF channel that correspond to the different regions.

In some embodiments, the pixel-level data acquired by the BF channel and the DF channel includes image data. In one such embodiment, the method includes aligning the image data acquired by the BF channel to the image data acquired by the DF channel and using the aligned image data to identify the defects that are real defects and the defects that are nuisance events. In such an embodiment, the pixel level-data may be acquired by the BF channel and the DF channel for process window qualification (PWQ).

In another embodiment, the method includes clustering the combined data into different groups based on one or more characteristics of the combined data. In one such embodiment, detecting the defects includes applying different values of the two-dimensional threshold to the different groups. In a further embodiment, the pixel-level data acquired by the BF channel and the DF channel includes image data. In one such embodiment, the method includes clustering the combined data into different groups based on one or more features extracted from the image data. In such an embodiment, detecting the defects may include applying different values of the two-dimensional threshold to the different groups.

In some embodiments, the method includes determining a size of the defects using the pixel-level data acquired by the BF channel or the DF channel and filtering the defects based on the size. In another embodiment, detecting the defects as described above is performed for one region of a die formed on the specimen. In one such embodiment, the method includes detecting the defects in a different region of the die on the specimen by applying the threshold for the data acquired by the BF channel or the DF channel to the pixel-level data acquired by the BF channel or the DF channel, respectively. Each of the embodiments of the method described above may include any other step(s) described herein.

Another embodiment relates to a carrier medium that includes program instructions. The program instructions are executable on a computer system for performing a method for detecting defects on a specimen. The method includes combining pixel-level data acquired for the specimen by a BF channel and a DF channel of an inspection system. The method also includes detecting defects on the specimen by applying a two-dimensional threshold to the combined data. The two-dimensional threshold is defined as a function of a threshold for the data acquired by the BF channel and a threshold for the data acquired by the DF channel. The method that is executable by the program instructions may include any other step(s) of any other method(s) described herein. The carrier medium and the program instructions may be further configured as described herein.

An additional embodiment relates to a system configured to detect defects on a specimen. The system includes an inspection system that includes a BF channel and a DF channel. The BF channel and the DF channel are configured to acquire pixel-level data for the specimen. The system also includes a processor configured to combine the pixel-level data acquired for the specimen by the BF channel and the DF channel. The processor is also configured to detect defects on the specimen by applying a two-dimensional threshold to the combined data. The two-dimensional threshold is defined as a function of a threshold for the data acquired by the BF channel and a threshold for the data acquired by the DF channel. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
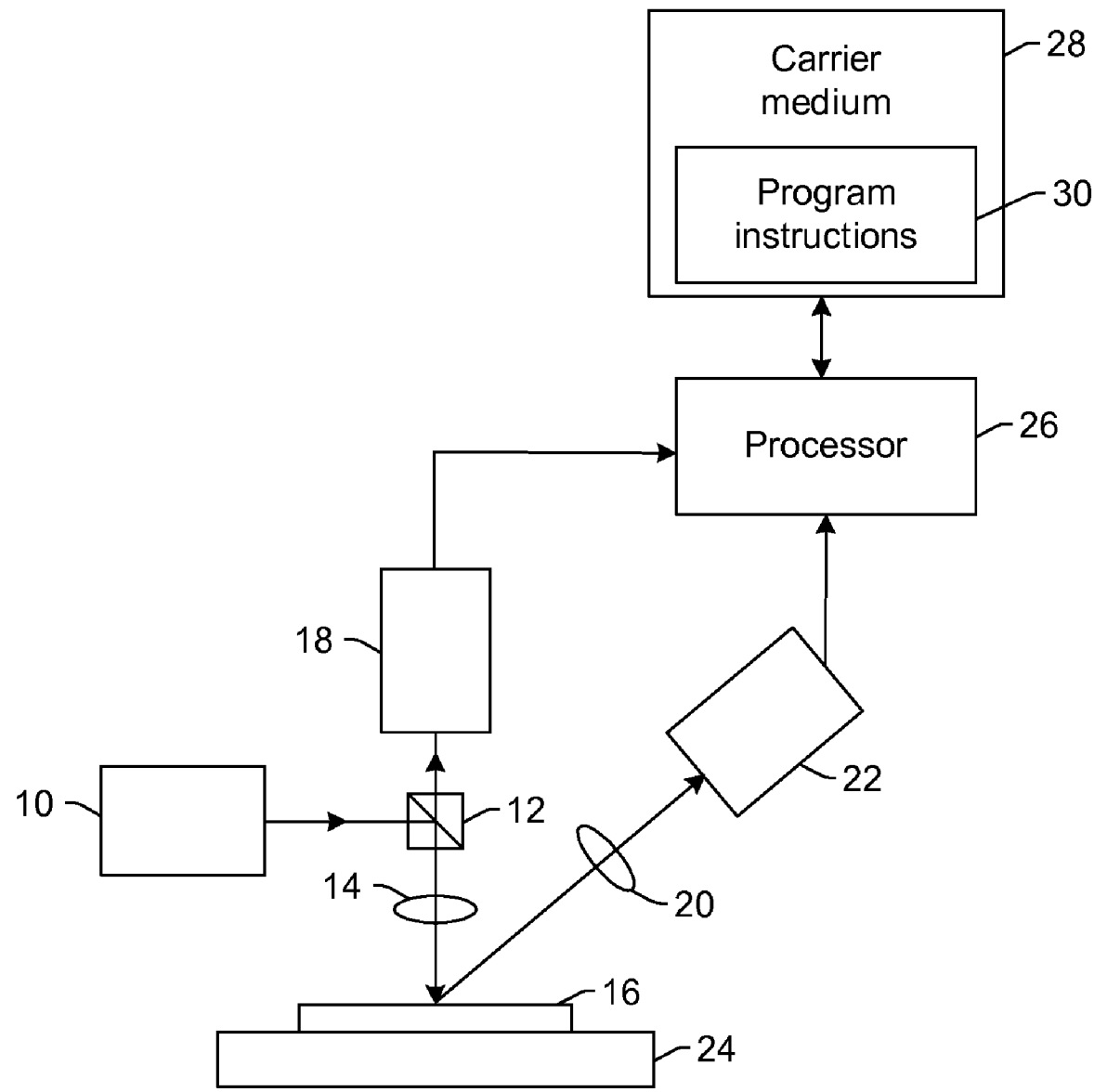
FIG. 1 is a schematic diagram illustrating a side view of one embodiment of a carrier medium that includes program instructions executable on a computer system for performing a method for detecting defects on a specimen and one embodiment of a system configured to detect defects on a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer, a photomask, or a reticle. However, it is to be understood that the methods, carrier media, and systems described herein may be used for detecting defects on any other specimen known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

The terms "reticle" and "photomask" are used interchangeably herein. A reticle generally includes a transparent substrate such as glass, borosilicate glass, and fused silica having opaque regions formed thereon. The opaque regions may be replaced by regions etched into the transparent substrate. Many different types of reticles are known in the art, and the term reticle as used herein is intended to encompass all types of reticles.

The term "design data" as used herein generally refers to the physical design (layout) of a device such as an integrated circuit (IC) being formed on a specimen and data derived from the physical design through complex simulation or simple geometric and Boolean operations.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to detect defects on a specimen. The system includes an inspection system. The inspection system includes a bright field (BF) channel and a dark field (DF) channel. The BF channel and the DF channel are configured to acquire pixel-level data for the specimen. It is noted that FIG. 1 is provided herein to generally illustrate one embodiment of a configuration for an inspection system that may be included in the system. Obviously, the system configuration described herein may be altered to optimize the performance of the system as is normally performed when designing a commercial inspection system. In addition, the systems described herein may be implemented using an existing inspection system (e.g., by adding functionality described herein to an existing inspection system). For some such systems, the defect detection methods described herein may be provided as optional functionality of the system (e.g., in addition to other functionality of the system). Alternatively, the system described herein may be designed "from scratch" to provide a completely new system.

The inspection system shown in FIG. 1 includes light source 10 (i.e., an illumination source). Light source 10 may include any appropriate light source known in the art. The inspection system may also include two or more light sources (not shown). The two or more light sources may be configured similarly or differently. For example, the light sources may be configured to generate light having different characteristics (e.g., wavelength, polarization, etc.) that can be directed to a specimen at the same or different angles of incidence and at the same or different time.

Light source 10 is configured to direct light to beam splitter 12. Beam splitter 12 is configured to direct light from light source 10 to objective 14. Objective 14 is configured to focus the light from beam splitter 12 onto specimen 16 at a substantially normal angle of incidence. However, the inspection system may be configured to direct the light to the specimen at any suitable angle of incidence. Beam splitter 12 may include any appropriate optical component known in the art. Objective 14 may include any appropriate refractive optical component known in the art. In addition, although objective 14 is shown in FIG. 1 as a single refractive optical component, it is to be understood that objective 14 may include one or more refractive optical components and/or one or more reflective optical components.

The inspection system includes a collection system that includes multiple, independent detection channels. Each detection channel is configured to collect light scattered or reflected from the specimen under test over a unique set of collection angles. In addition, although embodiments are described further herein as including a BF channel and a DF channel, it is to be understood that the inspection system embodiments described herein may include any combination of two or more detection channels (e.g., one BF channel and one or more DF channels). Moreover, the inspection systems described herein may include a number of detection channels, and data acquired by all of the detection channels or fewer than all of the detection channels may be used by a processor as described further herein. The data acquired by a particular combination of detection channels that is used by a processor as described further herein may be selected based on, for example, characteristics of the specimen, characteristics of the defects of interest, and characteristics of the inspection system.

In the embodiment shown in FIG. 1, light reflected from specimen 16 is collected by objective 14 and passes through beam splitter 12 to detector 18. Detector 18 may include any appropriate detector known in the art. Detector 18 is configured to acquire pixel-level data for specimen 16. In addition, detector 18 may include an imaging detector. Therefore, the pixel-level data acquired by detector 18 may include image data. As shown in FIG. 1, objective 14 is configured to collect light specularly reflected from the specimen, and detector 18 is configured to detect light specularly reflected from the specimen. Therefore, objective 14 and detector 18 form the BF channel of the inspection system. As such, the BF channel of the inspection system is configured to acquire pixel-level data for the specimen. In addition, the BF channel of the inspection system may be configured to acquire pixel-level data that includes image data.

Light scattered from specimen 16 is collected by objective 20, which directs the collected light to detector 22. Objective 20 may include any appropriate refractive optical component known in the art. In addition, although objective 20 is shown in FIG. 1 as a single refractive optical component, it is to be understood that objective 20 may include one or more refractive optical components and/or one or more reflective optical components. Objective 20 may be configured to collect light scattered from the specimen at any suitable scattering angles. In addition, the scattering angles at which objective 20 is configured to collect light scattered from the specimen may be determined based on one or more characteristics (e.g., of patterned features (not shown) or defects of interest (not shown)) of the specimen.

Detector 22 may include any appropriate detector known in the art. Detector 22 is configured to acquire pixel-level data for specimen 16. In addition, detector 22 may include an imaging detector. Therefore, the pixel-level data acquired by detector 22 may include image data. As shown in FIG. 1, objective 20 is configured to collect light scattered from the specimen, and detector 22 is configured to detect light scattered from the specimen. Therefore, objective 20 and detector 22 form the DF channel of the inspection system. As such, the DF channel of the inspection system is configured to acquire pixel-level data for the specimen. In addition, the DF channel of the inspection system may be configured to acquire pixel-level data that includes image data.

In some embodiments, the BF channel and the DF channel are configured to acquire the pixel-level data in the deep ultraviolet (DUV) spectrum. For example, light source 10 may be configured to generate light in the DUV spectrum. In addition, detectors 18 and 22 may be configured to detect light reflected and scattered, respectively, in the DUV spectrum. However, the BF and DF channels may also or alternatively be configured to acquired the pixel-level data in any other suitable spectrum (e.g., ultraviolet (UV) and/or visible).

During acquisition of the data by the BF and DF channels of the inspection system, specimen 16 may be disposed on stage 24. Stage 24 may include any appropriate mechanical and/or robotic assembly known in the art (e.g., a scanning stage configured to support the specimen under test).

The system also includes processor 26. Processor 26 may be coupled to detectors 18 and 22 such that the processor can receive pixel-level data from detectors 18 and 22. Processor 26 may be coupled to the detectors in any suitable manner known in the art (e.g., via a transmission medium (not shown) that may include "wired" and/or "wireless" portions, via electronic components (not shown) interposed between each of the detectors and the processor, etc.).

Processor 26 is configured to combine the pixel-level data acquired for the specimen by the BF channel and the DF channel. The processor may be configured to combine the pixel-level data as described further herein. The processor is also configured to detect defects on the specimen by applying a two-dimensional threshold to the combined data. The two-dimensional threshold is defined as a function of a threshold for the data acquired by the BF channel and a threshold for the data acquired by the DF channel. The processor may be configured to detect the defects on the specimen as described further herein. The processor may also be configured to perform any other step(s) of any other method(s) described herein.

Processor 26 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The inspection system shown in FIG. 1 may also include any other suitable components (not shown) known in the art. Furthermore, the inspection system shown in FIG. 1 may be replaced with a commercially available inspection system such as the 2360, 2365, 2371, and 23xx systems that are available from KLA-Tencor, San Jose, Calif. The embodiments of the system shown in FIG. 1 may be further configured as described herein. In addition, the system may be configured to perform any other step(s) of any of the method embodiments described herein. The embodiments of the system shown in FIG. 1 have all of the advantages of the method embodiments described herein.

FIG. 1 also illustrates one embodiment of carrier medium 28 that includes program instructions 30 executable on a computer system (e.g., processor 26) for performing a method for detecting defects on specimen 16. The method includes combining pixel-level data acquired for the specimen by the BF channel and the DF channel of the inspection system. Combining the pixel-level data may be performed as described herein. The method also includes detecting defects on the specimen by applying a two-dimensional threshold to the combined data. The two-dimensional threshold is defined as a function of a threshold for the data acquired by the BF channel and a threshold for the data acquired by the DF channel. Detecting the defects may be performed as described herein. In addition, the method for which program instructions 30 are executable may include any other step(s) of any other method(s) described herein.

Program instructions 30 implementing methods such as those described herein may be transmitted over or stored on carrier medium 28. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

As described above, the program instructions may be executable on processor 26. Therefore, the program instructions may be executable on a processor or a computer system coupled to an inspection system. However, the program instructions may be executable on a processor or a computer system that is not coupled to an inspection system. In this manner, the carrier medium and the processor or computer system may be configured as a "stand alone" system. The stand alone system may, however, be configured to acquire the pixel-level data described above from an inspection system (e.g., from a processor or storage medium of the inspection system). The stand-alone system may acquire the inspection data in any manner known in the art (e.g., via a transmission medium that may include "wired" and/or "wireless" portions). In this manner, the transmission medium may serve as a data link between the processor and the inspection system. Therefore, the methods described herein may or may not include acquiring the pixel-level data by performing inspection of a specimen. In other words, the methods described herein may be performed by a system that does not include an inspection system.

In one embodiment, the pixel-level data is acquired by the BF channel and the DF channel for process window qualification (PWQ). PWQ applications for lithography generally involve exposing different dies on a wafer at different exposure dosages and focus offsets (i.e., at modulated dose and focus) and identifying systematic defects in the dies that can be used to determine areas of design weakness and the process window. Examples of PWQ applications for lithography are illustrated in U.S. patent application Ser. No. 11/005,658 filed Dec. 7, 2004 by Wu et al., which is incorporated by reference as if fully set forth herein. Many artifacts of focus and exposure modulation can appear as defects (die-to-reference die differences), but are in fact nuisance defects. Examples of such artifacts may include critical dimension (CD) variations and line-end pullbacks in regions in which these artifacts have no impact on yield or performance. The embodiments of the carrier medium described above have all of the advantages of the corresponding method embodiments described herein.

Another embodiment relates to a computer-implemented method for detecting defects on a specimen. In general, the methods described herein can be used to improve the performance of inspection or an inspection system by combining or by using in combination the data acquired by two or more independent detection channels of the inspection system such as a BF channel and a DF channel (e.g., operating at the DUV spectrum) to optimize the sensitivity, accuracy, and/or purity of the inspection results. In addition, the methods described herein may be used to improve the overall sensitivity of inspection by using the information from one channel to modulate the data in another channel thereby improving the value and reliability of the data in either channel individually.

Although various embodiments are described herein with respect to data acquired by a BF channel and a DF channel, it is to be understood that the methods described herein may be performed using data acquired by any combination of two or more independent detection channels of an inspection system (e.g., a BF channel and one or more DF channels). In addition, the methods described herein may be performed using data acquired by all of the detection channels of an inspection system or fewer than all of the detection channels. The data acquired by a particular combination of detection channels that is used in the method embodiments described herein may be selected based on, for example, characteristics of the specimen, characteristics of the defects of interest, and characteristics of the inspection system.

The method includes combining pixel-level data acquired for the specimen by a BF channel and a DF channel of an inspection system. The inspection system may be configured as described above. In one embodiment, the pixel-level data is acquired by the BF channel and the DF channel in the DUV spectrum. However, it is to be understood that the pixel-level data may also or alternatively be acquired by the BF and DF channels in any other spectrum (e.g., UV, visible, etc.). Combining the pixel-level data acquired by the BF and DF channels may be performed based on the position on the specimen at which the data was acquired by the BF and DF channels. In other words, BF channel data and DF channel data acquired at the same position on the specimen may be combined. The combined data may be stored or used in any suitable format known in the art (e.g., such as a plot described further below).

Figure 2:
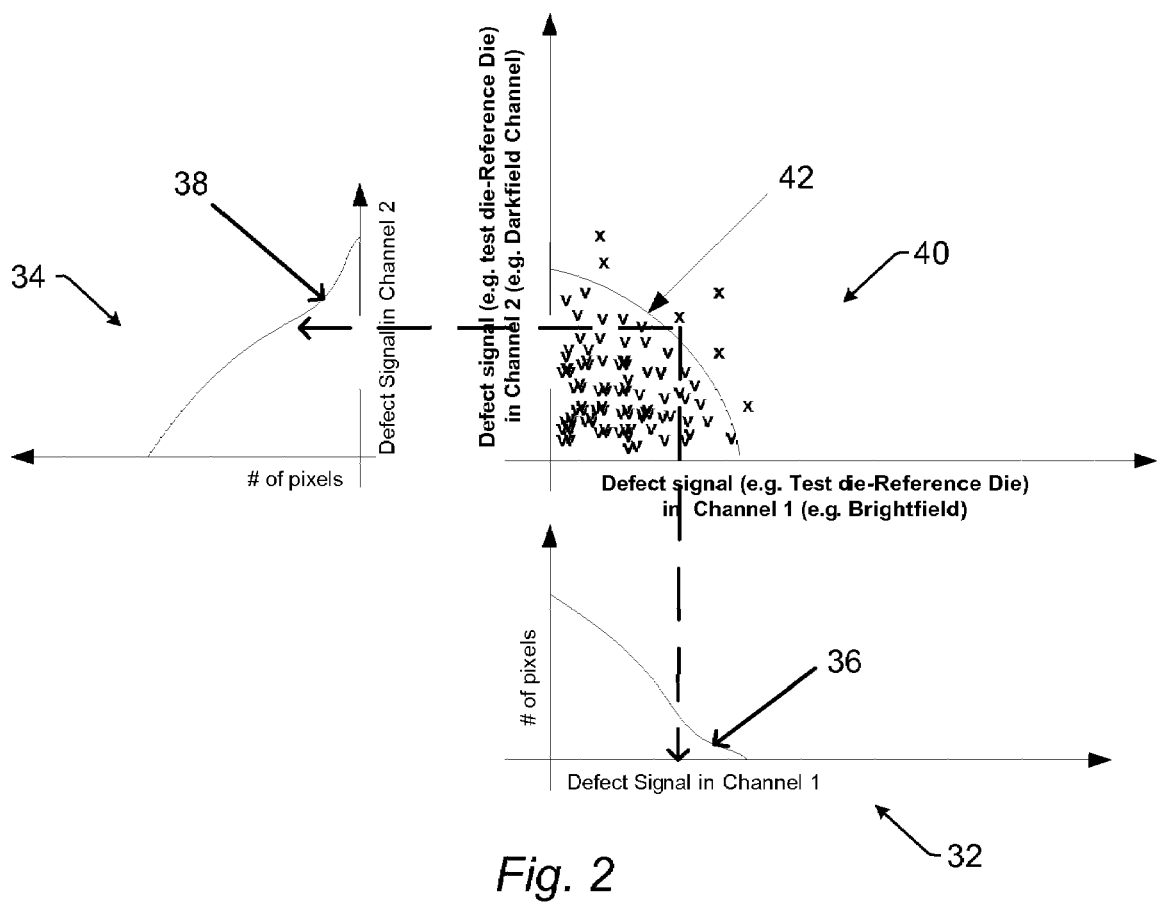
FIG. 2 includes plots illustrating one embodiment of combined pixel-level data acquired for a specimen by a bright field channel and a dark field channel of an inspection system and a two-dimensional threshold applied to the combined data.

The method also includes detecting defects on the specimen by applying a two-dimensional threshold to the combined data. The two-dimensional threshold is defined as a function of a threshold for the data acquired by the BF channel and a threshold for the data acquired by the DF channel. In other words, the two-dimensional threshold is defined in two-dimensional space. One embodiment of combined pixel-level data and a two-dimensional threshold are illustrated in FIG. 2. As shown in FIG. 2, in previously used methods for detecting defects on a specimen, the pixel-level data for one channel is plotted as a function of pixel number in plots 32 and 34. In particular, defect signal in channel 1 as a function of number of pixels is shown in plot 32. Channel 1 in this instance is the BF channel. Defect signal in channel 2 as a function of number of pixels is shown in plot 34. Channel 2 in this example is the DF channel.

The "defect signal" values shown in these plots is pixel-level data generated by subtracting BF reference data from raw data acquired by the BF channel and subtracting DF reference data from raw data acquired by the DF channel. The BF and DF reference data may include any suitable reference data known in the art such as a reference die. Therefore, the "defect signal" values shown in these plots are not signals that have been determined to correspond to defects.

Instead, a threshold is applied to the defect signal values that are shown in the plots. For example, threshold 36 for data acquired by channel 1 is applied to the data shown in plot 32. In addition, threshold 38 for data acquired by channel 2 is applied to the data shown in plot 34. Thresholds 36 and 38 are one-dimensional thresholds in that the thresholds are defined by values for data acquired by either channel 1 or channel 2 as a function of pixel number. In other words, thresholds 36 and 38 vary in only one dimension (i.e., values of the data). By applying threshold 36 to the data acquired by channel 1, outliers or defects cannot be detected without also detecting nuisance defects. Similarly, by applying threshold 38 to the data acquired by channel 2, outliers or defects cannot be detected without also detecting nuisance defects.

In one embodiment, however, plot 40 is generated from the defect signal values acquired by channel 1 (e.g., the bright field channel) as a function of the defect signal values acquired by channel 2 (e.g., the dark field channel). In particular, each of the data points (x and v) shown in plot 40 may be determined by the defect signal values acquired by channel 1 and 2 at the same pixel number. Therefore, the data points shown in plot 40 are the combined data acquired by the BF and DF channels.

In one embodiment, the methods described herein include generating the pixel-level data by subtracting BF reference data from raw data acquired by the BF channel and subtracting DF reference data from raw data acquired by the DF channel. For example, the defect signal values shown in these plots can be determined by subtracting reference die data from test die data. In addition, reference data may be subtracted from raw data in the methods described herein using any suitable method or system known in the art. Therefore, the "defect signal" values shown in these plots are not signals that have been determined to correspond to defects.

Two-dimensional threshold 42 is applied to the combined data. The two-dimensional threshold is defined as a function of thresholds 36 and 38. The two-dimensional threshold may have any suitable form known in the art such as a discriminate function. As shown in FIG. 2, if two-dimensional threshold 42 is applied to the combined data shown in plot 40, the combined data corresponding to outlier (defective) pixels (x) are located outside of the boundary defined by two-dimensional threshold 42 and are, therefore, detected as defects. In contrast, the combined data corresponding to non-outlier pixels (v) are located inside of the boundary defined by two-dimensional threshold 42 and are, therefore, not detected as defects. Therefore, the two-dimensional threshold can be applied to the combined data to detect defects and not nuisance defects with relatively high accuracy. In this manner, the BF channel data and the DF channel data can be combined and processed collectively at the pixel-level to improve the signal-to-noise ratio for defect detection. Such combining and collection processing of the BF and DF channel data is particularly advantageous for increasing the signal-to-noise ratio for defect detection in the DUV spectrum.

As described further above, using the data acquired by only channel 1 or channel 2 to detect defects causes nuisance defects to also be detected. In particular, by applying a one-dimensional threshold to data acquired by a corresponding channel, defect outliers (x) cannot be detected without also detecting nuisance defects (v). Obviously, detecting nuisance defects is disadvantageous for many reasons known in the art. In contrast, as described above, applying the two-dimensional threshold to the combined data produces a defect population that includes real defects and not nuisance defects. In other words, combining defect signals from both channels allows for detecting outliers (defective pixels) without detecting nuisance events. Therefore, applying the two-dimensional threshold to the combined data results in a signal-to-noise ratio for detecting the defects that is higher than a signal-to-noise ratio for detecting the defects by applying the threshold for the data acquired by the BF channel to the pixel-level data acquired by the BF channel and by applying the threshold for the data acquired by the DF channel to the pixel-level data acquired by the DF channel. In addition, the defects detected using the two-dimensional threshold include fewer nuisance defects than defects detected by applying the threshold for the data acquired by the BF channel to the pixel-level data acquired by the BF channel and by applying the threshold for the data acquired by the DF channel to the pixel-level data acquired by the DF channel.

As described above, combined BF and DF pixel-level data and a two-dimensional threshold may be advantageously used to increase the sensitivity, accuracy, and purity of defect detection results. In addition, the BF and DF pixel-level data may also be advantageously used in combination for other defect-related functions. For example, in one embodiment, the method includes classifying the defects using one or more characteristics of the combined data corresponding to the defects (e.g., features of the BF and DF "blobs" such as size, maximum density, etc.), one or more characteristics of patterned features formed on the specimen proximate to the defects determined from pixel-level data acquired by the BF channel (e.g., features of the context in the BF data), one or more characteristics of the patterned features formed on the specimen proximate to the defects determined from the pixel-level data acquired by the DF channel (e.g., features of the context in the DF data), or some combination thereof. The features of the context in the BF and/or DF data may be extracted using any appropriate feature extraction method known in the art. Examples of feature extraction methods are illustrated in U.S. Pat. No. 6,104,835 to Han, U.S. Pat No. 6,650,779 to Vachtesvanos et al., U.S. Pat No. 6,804,381 to Pan et al., and U.S. Pat No. 6,855,930 to Okuda et al., which are incorporated by reference as if fully set forth herein. The methods and systems described herein may use any of the methods described in these patents to extract features of the context in the BF data and/or the DF data. Therefore, the method embodiments described herein may include defect classification through cross-channel background binning.

The BF and DF blob and/or context features may be used to improve the classification of defects by type. For example, the performance of inspection or an inspection system may be improved by combining the data from two or more independent detection channels such as a BF channel and a DF channel (e.g., operating at the DUV spectrum) to optimize the accuracy and/or purity of binning results of the inspection or the inspection system. In addition, the methods described herein may be used to improve the overall binning performance by using the information from one channel to modulate the data in another channel to improve the value and reliability of the data in either channel individually.

Although detecting defects as described in the above embodiments is advantageous for at least the reasons set forth above, the defects that are classified as described above may or may not be detected as described above. For instance, the defects that are classified as described above may be detected by applying a one-dimensional threshold to data acquired by only one of the channels of the inspection system. In such an instance, the data to which the one-dimensional threshold is applied may be generated by comparing the raw data acquired by the channel for one die on the specimen to a reference die. However, regardless of how the defects are detected, for defects that are detected at substantially the same location by two or more channels of the inspection system, classification may be performed using a combination of information determined from the data acquired by the two or more channels. In all other steps described herein (other than the defect detection steps described above), the defects may be detected in any suitable manner known in the art.

In another embodiment, the method includes altering the threshold for the data acquired by the BF or DF channel based on the pixel-level data acquired by the DF or BF channel, respectively. In this manner, the pixel-level data acquired by one of the channels of the inspection system can be used to alter the threshold for the data acquired by another channel of the inspection system. In addition, the threshold may be altered depending on information about different areas on the specimen that can be identified or determined from the data acquired by one of the channels. For example, the data acquired by the BF channel may be used to determine and "mask out" certain areas on the specimen as "do not care" areas (i.e., as opposed to "care areas" or the areas of the device pattern formed on the specimen in which inspection will be performed). Therefore, inspection data may not be acquired in do not care areas, or defect detection may not be performed on inspection data acquired in the do not care areas. Although the data acquired by the BF channel generally includes a substantial amount of information about patterned features on the specimen that makes this data particularly useful for locating the care areas, the data acquired by the DF channel may also include sufficient information about the patterned features such that the DF data can be used for care area location.

The information about the areas on the specimen that can be determined from data acquired by one channel and that may be used to alter the threshold applied to data acquired by another channel may, therefore, include information about the location of care areas and do not care areas on the specimen. In addition, the information about the areas on the specimen may include information about the location of critical areas and non-critical areas on the specimen. In this manner, the threshold, and therefore the sensitivity of the inspection process, can be altered depending on whether the data is acquired in a care area on the specimen, a do not care area on the specimen, a critical area on the specimen, and a non-critical area on the specimen.

In another example, the threshold applied to data acquired by the DF channel can be increased if, for example, the corresponding data in the BF channel exhibits a strong signal, which may be indicative of a highly reflective surface. Such a highly reflective surface may create a significant amount of noise in the DF channel. Therefore, when the BF channel exhibits a number of relatively bright pixels, the threshold for the corresponding pixels in the DF channel can be increased such that noise in the DF channel is not erroneously detected as defects. Altering the threshold in this manner can also reduce the number of nuisance defects included in the overall defect population since a higher threshold can be applied to data acquired at the locations on the specimen in which nuisance defects may be located or are predominant (versus real defects).

Furthermore, the threshold for data acquired by one channel can be determined from the data acquired by another channel in real time (e.g., during inspection of the specimen or during acquisition of the pixel-level data). Therefore, the data acquired by one of the channels of the inspection system may be used for dynamic care area generation. Such dynamic care area generation or identification may be advantageous for a number of reasons. For instance, the location of care areas on the specimen may be difficult to determine accurately prior to inspection using other information such as information about the device design being printed on the specimen and information about where on the specimen the device design is supposed to be printed. In particular, the location of the different care areas may vary significantly based on, for example, the alignment of the specimen in the processes used to print the device design on the specimen, the alignment of the specimen in the inspection system, and thermal or mechanical variations in the stage in the inspection system used to support the specimen.

The embodiments described herein can, therefore, be used for automatic care area definition at the pixel level (e.g., by using pixel-level data), which avoids care area border uncertainty (due to user errors and system mechanical errors) in defining care areas and eliminates the user having to define care areas (which is a tedious process). For example, to account for the positional inaccuracy of the care areas on the specimen, often a predefined care area may include a relatively wide care area border. Ambiguity in the care area border (e.g., a border uncertainty having a spread of about 5 µm or more) can result in different areas being inspected with the incorrect threshold thereby reducing the accuracy and the overall sensitivity of the inspection. However, in the methods described herein, the care areas can be defined substantially precisely based on the data acquired by one of the channels of the inspection system thereby increasing the accuracy with which the appropriate threshold is applied to the pixel-level data acquired by another channel or other channels of the inspection system thereby increasing the accuracy and the overall sensitivity of the inspection.

In another embodiment, the method includes using the pixel-level data acquired by the BF channel to align the pixel-level data acquired by the BF channel to design data for the specimen. Such an embodiment may also include altering the threshold for the data acquired by the BF channel based on the design data. In an additional embodiment, the method includes using the pixel-level data acquired by the BF channel to align the pixel-level data acquired by the DF channel to design data for the specimen and altering the threshold for the data acquired by the DF channel based on the design data. In this manner, the methods described herein enable "align to design" for data acquired by the BF and/or DF channels using the resolution of patterned features printed on the specimen provided by the BF channel.

In other words, the data acquired by the BF channel may be used to align data acquired by one or more channels of the inspection system to design data (e.g., data in a design database). For instance, a substantial amount of information about a device pattern formed on the specimen may be acquired from the data acquired by the BF channel. Such information about the device pattern may then be used to align the data acquired by the BF channel to the design data. The pixel-level data acquired by the DF channel may be aligned to the data acquired by the BF channel on a pixel-to-pixel basis as described further herein thereby effectively aligning the data acquired by the DF channel to the design data.

In a similar manner, the method may include using the pixel-level data acquired by the DF channel to align the pixel-level data acquired by the DF and/or BF channel to design data for the specimen. For example, the pixel-level data acquired by the DF channel may include strong scattering signals from the edges of features formed on the specimen. The information about the edges of the features formed on the specimen may be used to align the pixel-level data acquired by the DF channel to the design data. The pixel-level data acquired by the BF channel may be aligned to the data acquired by the DF channel on a pixel-to-pixel basis as described further herein thereby effectively aligning the data acquired by the BF channel to the design data. Such an embodiment may also include altering the threshold for the data acquired by the DF and/or BF channel based on the design data. For example, the threshold may be altered based on one or more characteristics of the design data such as the regions in the design containing device features, the regions in the design containing test features, critical regions of the design, and the like.

The method embodiments described herein are, therefore, advantageous since information about the position of the acquired data with respect to the design data may be determined with relatively high accuracy (e.g., less than one pixel or sub-pixel accuracy). Examples of methods and systems for determining the location of inspection data in design data space are illustrated in U.S. Patent Application Ser. No. 60/738,290 by Kulkarni et al., filed on Nov. 18, 2005, which is incorporated by reference as if fully set forth herein. The positional information of the acquired data with respect to the design data may be used for sorting of the acquired data including, for example, selecting sensitive regions in the acquired data, reducing sensitivity in unimportant or non-critical regions, and background or context based binning of the defects. Examples of methods and systems for background or context based binning are also illustrated in this patent application. The methods and systems described herein may include any step(s) or may be configured to perform any step(s) of any of the methods described in this patent application.

In a further embodiment, the method includes identifying patterned features on the specimen using the pixel-level data acquired by the BF channel, separating the data acquired by the DF channel into different segments based on the patterned features, and altering the threshold for the data acquired by the DF channel for the different segments based on the patterned features. In a different embodiment, the method includes identifying patterned features on the specimen using the pixel-level data acquired by the DF channel, separating the data acquired by the BF channel into different segments based on the patterned features, and altering the threshold for the data acquired by the BF channel for the different segments based on the patterned features.

In the embodiments described above, therefore, the data acquired by one channel of the inspection system can be used to segment the data acquired by another channel by geometry and to alter the threshold for the segments (i.e., by segmented auto-thresholding (SAT)). The geometry or the patterned features can be identified in the data as described further above. Different thresholds may then be applied to each segment, which is advantageous as described above. In addition, the thresholds applied to each of the segments may be determined in real time (e.g., during inspection or during acquisition of the pixel-level data), which is advantageous as described further above. For example, the data acquired by the BF channel may be used to provide context/background information, and the data acquired by the DF channel can be used for detection of defects with different threshold values applied to different segments of the data acquired by the DF channel based on the context/background information. In another example, the data acquired by the DF channel may be used to provide context/background information, and the data acquired by the BF channel can be used for detection of defects with different threshold values applied to different segments of the data acquired by the BF channel based on the context/background information. The embodiments described above, therefore, include cross-channel SAT. In this manner, different threshold values and therefore different sensitivities can be used to detect defects in different segments of the acquired data.

In some embodiments, the pixel-level data acquired by the BF channel includes image data. In one such embodiment, the method includes comparing the image data to reference templates corresponding to different regions of the specimen to determine if the reference templates match the image data. Such an embodiment may also include using the image data matched to the reference templates to determine portions of the pixel-level data acquired by the DF channel that correspond to the different regions. In this manner, the method may include using the images acquired by the BF channel to perform template matching to identify certain pre-selected geometries in the images. The located geometries or "hits" in the data acquired by the BF channel may then be used to locate those same geometries in the data acquired by the DF channel. In addition, the locations of the geometries in the data acquired by the DF channel may be determined substantially exactly. The threshold values that are applied to the data acquired by the DF channel may be determined based on the locations of the geometries. Altering the threshold may be further performed as described above after the patterned features have been identified by template matching. In this manner, the threshold values and therefore the sensitivity of inspection can be altered for different portions of the geometry printed on the specimen.

In general, template matching includes comparing a reference image known to contain a pre-selected geometry to a test image to determine if the test image also contains the pre-selected geometry. The reference image may be a BF patch image acquired at a known location of the pre-selected geometry on a specimen (e.g., a reference specimen). Alternatively, the reference image may be a simulated image that illustrates how the pre-selected geometry would be printed on the specimen. Examples of methods and systems that can be used to simulate such reference images are illustrated in U.S. patent application Ser. No. 11/226,698 filed Sep. 14, 2005 by Verma et al., which is incorporated by reference as if fully set forth herein. The methods and systems described herein may include any of the step(s) and may be configured to perform any step(s) of any of the methods described in this patent application. The test image may be a BF image of the specimen acquired during the inspection of the specimen. The test image may or may not be a patch image.

The reference image may also be compared to different portions of the test image by "sliding" the reference image over the test image. Identifying the pre-selected geometry in the test image may be performed by determining a correlation between the reference image and different portions of the test image. The location of the reference image in the test image that results in the best correlation may then be identified as the location of the pre-selected geometry in the test image. Template matching may be further performed as described in U.S. patent application Ser. No. 11/300,172 by Lin et al., filed Dec. 14, 2005, which is incorporated by reference as if fully set forth herein. The methods and systems described herein may include any of the step(s) and may be configured to perform any step(s) of any of the methods described in this patent application. In this manner, the method embodiments described herein may include cross-channel template matching and segmentation. Although data acquired by a DF channel may conceivably be used for template matching and segmentation as described above, the data acquired by the DF channel may not include enough information about the patterned features for template matching and segmentation.

In another embodiment, the pixel-level data acquired by the BF channel and the DF channel includes image data. In one such embodiment, the method includes aligning the image data acquired by the BF channel to the image data acquired by the DF channel (or vice versa). Such an embodiment may also include using the aligned image data to identify the defects that are real defects and the defects that are nuisance events. The methods described above may be particularly advantageous for embodiments in which the pixel-level data is acquired by the BF channel and the DF channel for PWQ.

The embodiments described herein may, therefore, include cross-channel filtering of defects for PWQ applications. In particular, in the embodiments described herein, the BF and DF images may be substantially perfectly registered to one another to filter nuisance events from real defects for PWQ applications. For example, nuisance events such as line-end pullbacks and CD variations may behave differently in BF and DF real defects such as shorts. In one such example, BF image data may be more sensitive to nuisance events such as line-end pullbacks and CD variations than DF image data. As such, if defects detected in the BF image data are not also detected by the DF channel, then the defects in the BF image data may be identified as potential nuisance events. Therefore, the combination of the BF and DF image data may be used to discriminate between nuisance events and real defects.

In one embodiment, the method includes clustering the combined data into different groups based on one or more characteristics of the combined data. In another embodiment, the pixel-level data acquired by the BF channel and the DF channel includes image data. In one such embodiment, the method includes clustering the combined data into different groups based on one or more features extracted from the image data. In this manner, the embodiments described herein may include cross-channel clustering. For example, the method may include clustering to group pixels into "segments" based on their intensities (for data acquired by the BF and DF channel) or other features extracted from the BF and DF image data. In addition, in some embodiments, clustering may be performed based on one or more characteristics of the combined data in combination with one or more features extracted from the image data. For example, for each pixel in a die, the characteristic(s) of the data acquired by the BF and DF channels and the extracted feature characteristics are available for clustering. The features may be extracted from the image data as described further above.

In some embodiments, the different groups of the combined data clustered as described above may be used to identify outliers as defective pixels. In particular, the method embodiments described herein may include performing clustering to identify outliers as defective pixels using different two-dimensional thresholds (e.g., different discriminate functions) for each "segment." In addition, regardless of how clustering is performed, detecting the defects in the methods described herein may include applying different values of the two-dimensional threshold to the different groups. For example, the pixels may be grouped into different segments as described above. Different threshold values may then be applied to each segment, group, or cluster, which is advantageous for at least the reasons described further above. In this manner, the embodiments described herein may include identifying defective pixels using cross-channel clustering.

Figure 3:
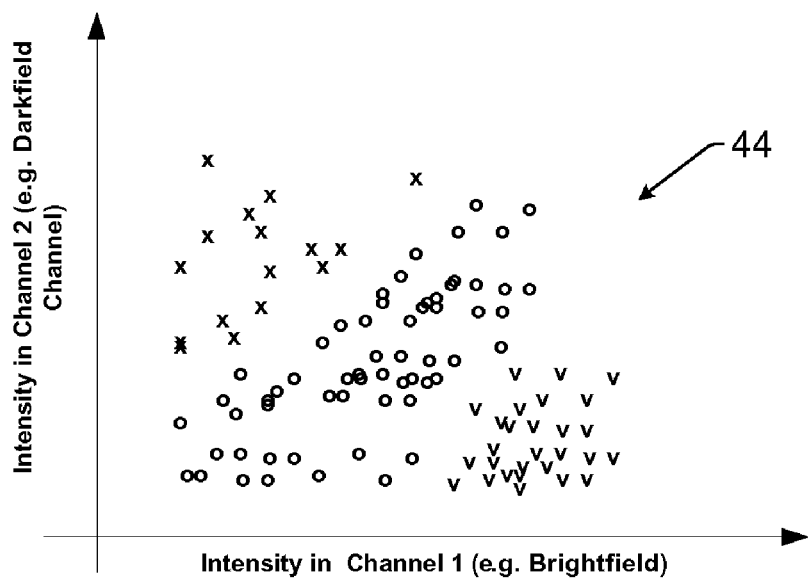
FIG. 3 is a plot illustrating one embodiment of combined data clustered into different groups based on one or more characteristics of the combined data.
Figure 4:
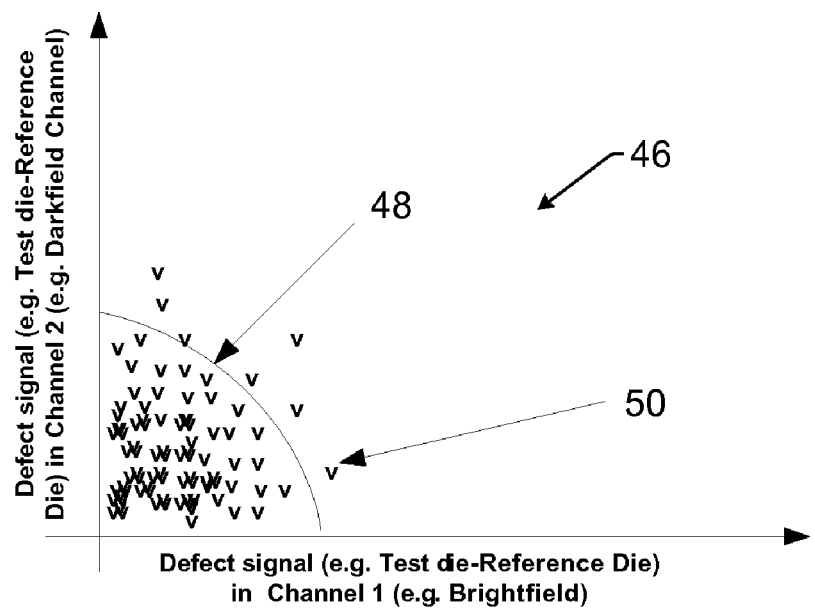
FIG. 4 is a plot illustrating one embodiment of a two-dimensional threshold applied to one of the different groups of FIG. 3.

One example of such an embodiment is illustrated in FIGS. 3 and 4. In particular, as shown in FIG. 3, the data acquired for the BF and DF channels may be combined in plot 44. In plot 44, intensity in channel 2 (e.g., the DF channel) is shown as a function of intensity in channel 1 (e.g., the BF channel). As shown in the plot, the combined data is clustered into three different groups, where one group of data points is shown by x's, another group of data points is shown by o's, and an additional group of data points is shown by v's. The different groups are segmented based on the intensity in channel 2 in combination with the intensity in channel 1. Therefore, the combined data is clustered based on the raw data acquired by the two channels.

One of the groups of combined data points is shown separately in FIG. 4. In particular, plot 46 illustrates the defect signal (e.g., test die-reference die) in channel 2 (e.g., the DF channel) as a function of the defect signal (e.g., test die-reference die) in channel 1 (e.g., the BF channel) for the group of data points shown by v's in FIG. 3. Two-dimensional threshold 48 is applied to the combined data, as described above. Two-dimensional threshold 48 may be further configured as described above. As shown in FIG. 4, outlier (defective) pixels including pixel 50 located outside of the two-dimensional threshold are detected as defects. In this manner, outlier pixels in the "v" cluster can be detected using the defect signals in the two channels. Therefore, the defects in individual groups of combined data may be detected by applying different values of a two-dimensional threshold to the combined data. The threshold values applied to the different groups may be determined as described above. In addition, a different threshold value (or discriminate function) may be applied to each of the individual groups of pixels. Such methods for detecting defects have all of the advantages of the methods for detecting defects described above.

In some embodiments, the method includes determining a size of the defects using the pixel-level data acquired by the BF channel or the DF channel. The size of the defects that is determined in these embodiments may include any dimension of the defects (e.g., diameter, width, length, height, depth). The size of the defects may be determined using any appropriate method for determining defect size known in the art. Such embodiments may also include filtering the defects based on the size. For example, the data acquired by the BF channel may be used to determine a size of the defects. The size of the defects may then be used as a filter for the defects detected in the data acquired by the DF channel.

Although the size of defects can usually be determined with greater accuracy from data acquired by the BF channel than from data acquired by the DF channel, the size of the defects can be determined from data acquired by the DF channel, and the determined size may be used to filter defects detected in data acquired by the BF channel. In addition, the size of defects determined using data acquired by one of the channels (BF or DF) may be used to calibrate the size of the defects determined by another of the channels. In this manner, the embodiments described herein may include cross-channel sizing and filtering.

In an additional embodiment, detecting the defects as described above is performed for one region of a die formed on the specimen. In one such embodiment, the method includes detecting the defects in a different region of the die on the specimen by applying the threshold for the data acquired by the BF channel or the DF channel to the pixel-level data acquired by the BF channel or the DF channel, respectively. In this manner, the methods described herein may include using cross-channels dedicated for region inspection.

Such embodiments may be used to optimize inspection in different regions of a die such as array, random, and periphery regions of the die. For example, the DF channel may be better suited for inspection of array regions of a die. In contrast, the BF channel of an inspection system may be better suited for random (logic) regions and periphery regions of the die. In this manner, the different channels of the inspection system may be used for inspection of the different regions for which each is most sensitive. The regions in the die may be determined using embodiments of the method described herein. Therefore, the regions in the die formed on the specimen may be determined dynamically and more accurately than other methods for determining approximate locations of the regions of the die formed on the specimen prior to inspection of the specimen. Such embodiments are also advantageous since the system resources (e.g., the image computer) may be better utilized. For example, the methods described herein may conserve image computing cycles by not having to use both algorithms (for random and array geometry) on every region of the die.

Further modifications and alternative embodiments of various aspects of the invention may be apparent to those skilled in the art in view of this description. For example, methods and systems for detecting defects on a specimen using a combination of bright field channel data and dark field channel data are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a specimen, comprising:
   using a computer system to perform the following steps of the method:
   combining pixel-level data acquired for the specimen by a bright field channel and a dark field channel of an inspection system; and
   detecting defects on the specimen by applying a two-dimensional threshold to the combined data, wherein the two-dimensional threshold is defined as a function of a threshold for the data acquired by the bright field channel and a threshold for the data acquired by the dark field channel.

2. The method of claim 1, wherein the data is further acquired by the bright field channel and the dark field channel in the deep ultraviolet spectrum.

3. The method of claim 1, wherein said applying the two-dimensional threshold results in a signal-to-noise ratio for said detecting that is higher than a signal-to-noise ratio for detecting the defects by applying the threshold for the data acquired by the bright field channel to the pixel-level data acquired by the bright field channel and by applying the threshold for the data acquired by the dark field channel to the pixel-level data acquired by the dark field channel.

4. The method of claim 1, wherein the defects detected using the two-dimensional threshold comprise fewer nuisance defects than defects detected by applying the threshold for the data acquired by the bright field channel to the pixel-level data acquired by the bright field channel and by applying the threshold for the data acquired by the dark field channel to the pixel-level data acquired by the dark field channel.

5. The method of claim 1, further comprising generating the pixel-level data by subtracting bright field reference data from raw data acquired by the bright field channel and subtracting dark field reference data from raw data acquired by the dark field channel.

6. The method of claim 1, further comprising classifying the defects using one or more characteristics of the combined data corresponding to the defects, one or more characteristics of patterned features formed on the specimen proximate to the defects determined from the pixel-level data acquired by the bright field channel, one or more characteristics of the patterned features formed on the specimen proximate to the defects determined from the pixel-level data acquired by the dark field channel, or some combination thereof.

7. The method of claim 1, further comprising altering the threshold for the data acquired by the bright field or dark field channel based on the pixel-level data acquired by the dark field or bright field channel, respectively.

8. The method of claim 1, further comprising using the pixel-level data acquired by the bright field channel to align the pixel-level data acquired by the bright field channel to design data for the specimen and altering the threshold for the data acquired by the bright field channel based on the design data.

9. The method of claim 1, further comprising using the pixel-level data acquired by the bright field channel to align the pixel-level data acquired by the dark field channel to design data for the specimen and altering the threshold for the data acquired by the dark field channel based on the design data.

10. The method of claim 1, further comprising identifying patterned features on the specimen using the pixel-level data acquired by the bright field channel, separating the data acquired by the dark field channel into different segments based on the patterned features, and altering the threshold for the data acquired by the dark field channel for the different segments based on the patterned features.

11. The method of claim 1, further comprising identifying patterned features on the specimen using the pixel-level data acquired by the dark field channel, separating the data acquired by the bright field channel into different segments based on the patterned features, and altering the threshold for the data acquired by the bright field channel for the different segments based on the patterned features.

12. The method of claim 1, wherein the pixel-level data acquired by the bright field channel comprises image data, the method further comprising comparing the image data to reference templates corresponding to different regions of the specimen to determine if the reference templates match the image data and using the image data matched to the reference templates to determine portions of the pixel-level data acquired by the dark field channel that correspond to the different regions.

13. The method of claim 1, wherein the pixel-level data acquired by the bright field channel and the dark field channel comprises image data, the method further comprising aligning the image data acquired by the bright field channel to the image data acquired by the dark field channel and using the aligned image data to identify the defects that are real defects and the defects that are nuisance events.

14. The method of claim 13, wherein the pixel-level data is further acquired by the bright field channel and the dark field channel for process window qualification.

15. The method of claim 1, further comprising clustering the combined data into different groups based on one or more characteristics of the combined data.

16. The method of claim 15, wherein said detecting comprises applying different values of the two-dimensional threshold to the different groups.

17. The method of claim 1, wherein the pixel-level data acquired by the bright field channel and the dark field channel comprises image data, the method further comprising clustering the combined data into different groups based on one or more features extracted from the image data.

18. The method of claim 17, wherein said detecting comprises applying different values of the two-dimensional threshold to the different groups.

19. The method of claim 1, further comprising determining a size of the defects using the pixel-level data acquired by the bright field channel or the dark field channel and filtering the defects based on the size.

20. The method of claim 1, wherein said detecting is performed for one region of a die formed on the specimen, the method further comprising detecting the defects in a different region of the die on the specimen by applying the threshold for the data acquired by the bright field channel or the dark field channel to the pixel-level data acquired by the bright field channel or the dark field channel, respectively.

21. A storage medium, comprising program instructions executable on a computer system for performing a method for detecting defects on a specimen, wherein the method comprises:

combining pixel-level data acquired for the specimen by a bright field channel and a dark field channel of an inspection system; and detecting defects on the specimen by applying a two-dimensional threshold to the combined data, wherein the two-dimensional threshold is defined as a function of a threshold for the data acquired by the bright field channel and a threshold for the data acquired by the dark field channel.

22. A system configured to detect defects on a specimen, comprising:

an inspection system comprising a bright field channel and a dark field channel, wherein the bright field channel and the dark field channel are configured to acquire pixel-level data for the specimen; and a processor configured to:

combine the pixel-level data acquired for the specimen by the bright field channel and the dark field channel; and detect defects on the specimen by applying a two-dimensional threshold to the combined data, wherein the two-dimensional threshold is defined as a function of a threshold for the data acquired by the bright field channel and a threshold for the data acquired by the dark field channel.

* * * * *